United States Patent [19]

Mashelkar et al.

[11] Patent Number: 5,851,546

[45] Date of Patent: Dec. 22, 1998

[54] POLYMER COMPOSITION FOR CONTROLLED RELEASE OF ACTIVE INGREDIENTS IN RESPONSE TO PH, AND A PROCESS OF PREPARING THE SAME

[75] Inventors: Raghunath Anant Mashelkar; Mohan Gopalkrishna Kulkarni; Rohini Nitin Karmalkar, all of Maharashtra, India

[73] Assignee: Council of Scientific & Industrial Research, New Delhi, India

[21] Appl. No.: 615,431

[22] Filed: Mar. 14, 1996

[30] Foreign Application Priority Data

Jun. 14, 1995 [IN] India ............................... 1096/DEL/95

[51] Int. Cl.$^6$ ................................ A61F 2/00; A61K 9/52
[52] U.S. Cl. ......................... 424/426; 424/457; 424/484; 424/486
[58] Field of Search ..................... 424/484, 426, 424/428, 433, 457, 468, 475, 486

[56] References Cited

U.S. PATENT DOCUMENTS

| 4,071,508 | 1/1978 | Steckler | 260/79.3 MU |
|---|---|---|---|
| 4,177,056 | 12/1979 | Mueller et al. | 71/93 |
| 4,304,591 | 12/1981 | Mueller et al. | 71/93 |
| 4,931,279 | 6/1990 | Bawa et al. | 424/427 |

OTHER PUBLICATIONS

Agyilirah, G.A., & Banker, G.S., *in Polymers for Controlled Drug Delivery*, CRC Press, Chapter 3 (1991).
Akashi, M., Beppu, K., Kikuchi, I., and Miyauchi, N., *J. Macromo. Sci.* (Chem.) A. 23:1233 (1986).
Chaves, M.S., and Arranz, F.,*Makromol. Chem.* 189:2269 (1988).
Fitch, R.M., Gajria, C., and Tarcha, P.J., *J. Colloid. Interface. Sci.* 71:107 (1979).
Saffran, M., Kumar, G.S., Savariar, C., and Burnham, J.C., *Science* 233:1081 (1988).
Shah, S.S., Kulkarni, M.G., & Mashelkar, R.A., *J. Appl. Polym. Sci.* 41:2437 (1990).
Siegel, R.A., Falamarzian, M., Firestone, B.A. and Moxley, B.C., *J. Controlled Release* 8:179 (1986).
Yean, L. , Bunel, C. and Varian, J.P., *Makromol. Chem.,* 191:1119 (1990).
Wilken, L.O., Kochlar, M.M., Bennett, D.P., and Cosgrove, F.P., *J. Pharm. Sci.* 51:484 (1962).

*Primary Examiner*—Nathan M. Nutter
*Attorney, Agent, or Firm*—Merchant, Gould, Smith, Edell, Welter & Schmidt

[57] ABSTRACT

The present invention provides a polymer for the controlled release of a pendent chain linked active ingredient, and a process for the preparation of such a polymer for the controlled release of an active ingredient in response to pH. The process involves selecting a vinyl monomer to which the active ingredient molecule is covalently linked through a pendent group, and selecting monomers bearing catalytic groups. The active ingredient-bearing monomer and the catalytic group-containing monomer are brought in juxtaposition either by complexation or molecular imprinting, and then polymerized with a hydrophilic monomer and crosslinker under an inert atmosphere with a suitable polymerization initiator.

23 Claims, 2 Drawing Sheets

5,851,546

POLYMER COMPOSITION FOR CONTROLLED RELEASE OF ACTIVE INGREDIENTS IN RESPONSE TO PH, AND A PROCESS OF PREPARING THE SAME

FIELD OF THE INVENTION

The present invention relates to a new polymer, its preparation and its employment for the controlled release of active ingredients in response to pH. The invention includes the preparation of the polymer and its application for the controlled release of molecules such as p-nitrophenol, p-nitro benzoic acid and p-amino benzoic acid. The invention is equally applicable for the controlled release of other active ingredients including drugs, pesticides, insecticides, herbicides, fungicides, or other molecule bearing appropriate functional groups that react with the polymer in the side chain and that are preferably released in a specific environment at a predetermined rate. The specific environment may be a pH range of about pH 5–10, preferably about pH 5.5–9, and more preferably about pH 6–7.8. The drugs so linked may be delivered in the gastrointestinal tract in a pH range of about pH 5.5–7.5. Similarly, pesticides and insecticides can be released in the pH range of about pH 5–8. The active ingredient can be released at a predetermined rate of a few minutes to several days depending on the polymer composition.

BACKGROUND OF THE INVENTION

Conventional enteric coated systems consist of the active ingredient coated with anionic polymers. These coatings resist disintegration and/or dissolution in the gastric media, but dissolve or disintegrate in the intestinal fluids (L. O. Wilken, Jr., M. M. Kochlar, D. P. Bennett and F. P. Cosgrove, *J. Pharm. Sci.* 51:484 (1962); H. Kitagawa, T. Satoh, T. Yokoshima and T. Nanbe, *Pharmacometrics* 5:1 (1971); K. Lehman and D. Dreher, *Int. J. Pharm. Tech.* 2:31 (1981)). However, many of the enteric coated products fail to perform because they either disintegrate in the stomach, excessively release the drug content, or fail to release adequate amounts of the active ingredient in the intestine (P. J. Tarcha, in *Polymers for Controlled Drug Delivery*, CRC Press, Chapter 3 (1991)).

Publications in the area of chemically linked drug delivery systems describe a number of active ingredients covalently linked to soluble, crosslinked or biodegradable polymers where the active ingredient is released by the hydrolytic or enzymatic cleavage of the labile bond (J. Kopecek and P. Rejmanova, in *Controlled Drug Delivery*, S. D. Bruce (ed.), Boca Raton, Fla., 81 (1983); S. S. Shah, M. G. Kulkarni & R. A. Mashelkar, *J. Appl. Polym. Sci.* 41:2437 (1990); M. Saffran, G. S. Kumar, C. Savariar and J. C. Burnham, *Science* 233:1081 (1988)). These systems can achieve higher loadings of the active ingredient, and decrease the side effects as compared to systems where the active ingredient is only physically incorporated into the polymer matrix.

The rate of release of the active ingredient depends on the cleavage of the labile bond which takes place either hydrolytically or enzymatically. The major limitations are that the hydrolytic cleavage often requires drastic conditions such as highly alkaline pH, while the enzymatic cleavage is unpredictable since the diffusion of the enzyme in the polymer cannot be accurately controlled. Attempts have been made to increase the rate of hydrolysis of the polymer-active ingredient bond by increasing the hydrophilicity of the polymer matrix, or by introducing groups such as imidazole and carboxyl to enhance the hydrolysis rates (M. S. Chaves and F. Arranz, *Makromol. Chem.* 189:2269 (1988); L. Yean, C. Bunel and J. P. Varian, *Makromol. Chem.* 191:1119 (1990); and R. M. Fitch, C. Gajria and P. J. Tarcha, *J. Colloid. Interface. Sci.* 71:107 (1979); M. Akashi, K. Beppu, I. Kikuchi and N. Miyauchi, *J. Macromol, Sci. (Chem.) A.* 23:1233 (1986)). However, the enhancement in the rate of hydrolysis was not very significant.

Conventional pH sensitive controlled release systems comprise hydrophilic polyelectrolyte polymers where the drug is dispersed in the matrix. The release takes place by swelling or shrinking of the polymer matrix in response to pH (R. A. Siegel, M. Falamarzian, B. A. Firestone and B. C. Moxley, *J. Controlled Release* 8:179 (1988); H. Park and J. R. Robinson, *Pharm. Res.* 7:816 (1990)). Again, since the drug is physically dispersed in the matrix there is a possibility of dose dumping, or the swelling of the anionic polymers may not take place under physiological conditions and the composition may not be able to release all the drug.

OBJECTS OF THE INVENTION

Consequently, it is a principal object of the present invention to provide a new chemically linked drug delivery system for the controlled release of the active ingredient under physiological conditions, which overcomes the disadvantages inherent in the drug delivery systems previously described.

A more specific object resides in the provision of a new chemically linked drug delivery system which eliminates the difficulties associated with conventional enteric coated systems like dose dumping in the stomach or slower release in the intestine.

Yet another object of the invention resides in providing a new drug delivery system which offers additional advantages such as enhanced release rates under intestinal pH conditions, ability to switch off or on the release in response to pH and reducing the toxicity of the active ingredient by chemical linking.

A further object of the invention relates to a new polymer composed of vinyl monomers bearing at least one imidazole, carboxylic acid and hydroxyl group in the pendent chain of the monomer, so arranged in the polymer structure by complexation with a transition metal ion such as $Co^{++}$ so that the groups remain in close proximity of one another after polymerization.

Yet another object of the invention relates to a process for preparing a polymer composition useful for the control release of active ingredients incorporated therein in response to certain predetermined conditions.

SUMMARY OF THE INVENTION

The above objects are achieved with the present invention which provides a novel polymer composed of at least one imidazole, carboxylic acid and hydroxy group in the pendent chain of the monomer, and a process for preparing a polymer composition useful for the controlled release of active ingredients incorporated therein in response to certain predetermined conditions.

DETAILED DESCRIPTION OF THE INVENTION

The novel polymeric composition of the present invention provides the controlled release of a pendent chain linked active ingredient, having the formula $$A_x \, B_y \, C_z \, S_q,$$

wherein:

A is a vinyl monomer with an imidazole-bearing functional group;

B is a vinyl monomer with a hydroxyl-bearing functional group;

C is a vinyl monomer with a carboxyl-bearing functional group; and

S is a vinyl monomer covalently bonded through an amide or ester bond with a hydroxyl, carboxyl or amino group of a biologically-active molecule; and $x+y+z+q=1$, and x, y, z, q vary such that $0<x<1$ and $0<q<1$, and y and z can vary between 0 to 1.

As an illustration, we have used polymers comprising 2-hydroxyethyl methacrylate, methacrylic acid and methacrylol histidine, N-vinyl imidazole, and the active ingredient linked vinyl monomer (S) in varying molar ratios, although the molar ratio 1:1:1 is the most ideal and most efficient one. A preferred combination is the monomers $A_x$, $B_y$ and $C_z$ in a molar ratio of 1:1:1 (hydroxyl-bearing monomer: carboxyl-bearing monomer: imidazole-bearing monomer), although $B_y$ and/or $C_z$ may or may not be part of the complex. It is noted that the scope of the invention is not restricted to the three monomers and the compositions described above.

Figure 1A:
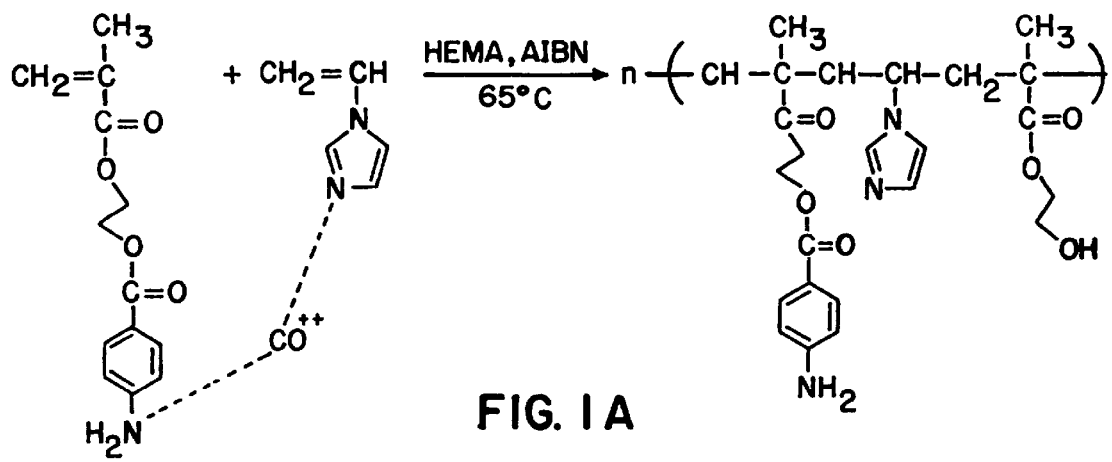
FIGS. 1A and 1B are schematic representations of reaction mechanisms consistent with one aspect of the invention.
Figure 1B:
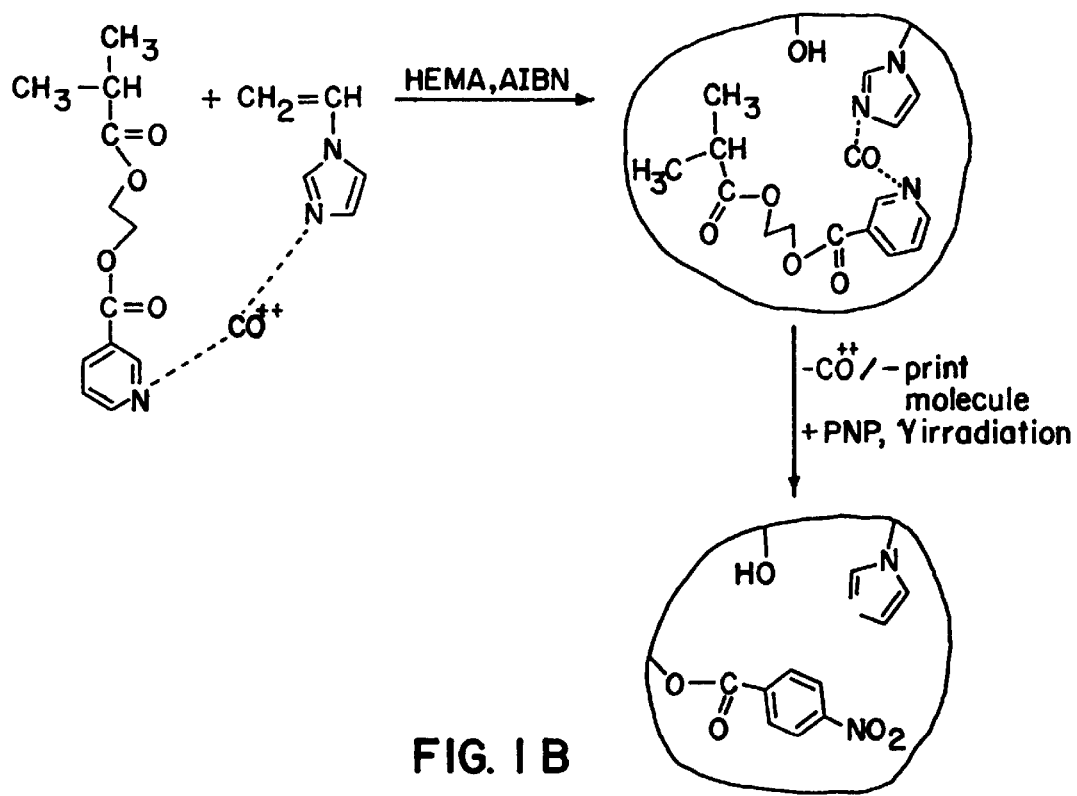

FIGS. 1A and 1B provide schematic diagrams of the polymerization steps for two different biologically active ingredient-linked monomer(s). As shown:

FIG. 1A p-amino benzoic acid is linked to 2-hydroxyethyl methacrylate to give 2-methacryloyl ethyl p-amino benzoate, the monomer $S_q$ (Example 9). The amino group of the monomer $S_q$ and the imidazole group of the monomer 1-vinyl imidazole ($A_x$) are complexed with cobalt in methanol. The hydrophilic monomer, 2-hydroxyethyl methacrylate, and the initiator azobisisobutyronitrile are added, and polymerization is initiated at 65° C.;

FIG. 1B p-nitrobenzoic acid is covalently bonded to 2-hydroxyethyl methacrylate to give 2-methacrylol ethyl p-nitrobenzoate ($S_q$ Example 6). The nitro group of 2-methyacrylol ethyl p-nitrobenzoate cannot form a complex with cobalt directly. Therefore, a print molecule or an analogue of $S_q$ is prepared which in the present case is 2-isobutyryl ethyl nicotinate. This is complexed with the monomer $A_x$ as described above. The hydrophilic monomer is then added and polymerized as described above at 65° C. The print molecule, i.e. isobutyryl ethyl nicotinate, and the cobalt are leached out in methanol. The monomer $S_q$ is then sorbed into the polymer disks from an acetone solution and polymerized by Y irradiation.

The present invention further provides a process for the preparation of a polymeric composition useful for the controlled release of the active ingredient incorporated therein in response to pH in the range of about pH 5.0 to 10, preferably about pH 5.0 to 9, or in the range of about pH 5.5 to 9, most preferably about pH 5.5 to 8, or 6.78 (see Table 1). This is because the catalytic activity of the polymer comprising the three monomers brought together in the vicinity of one another and to that of the active ingredient-linked monomer(s) by complexation with a metal ion prior to polymerization, is dependent on the pH and is lost below pH 3.5. The dependence of the catalytic activity on pH results mainly from the arrangement of the functional groups in the vicinity of one another and that of the active ingredient by complexation with a metal ion. A polymer composed of the same monomers but not prearranged as described herein, do not exhibit pH-dependent catalytic activity.

The active ingredient is bonded to a functional group at the end of a long chain of the vinyl monomer (i.e., pendent chain). The biologically-active molecule can be a drug, insecticide, fungicide, herbicide, pesticide, weedicide, and the like. This active ingredient is linked to the polymer through a hydroxyl (—OH), carboxyl (—COOH) or amino (—NH$_2$) functional group via amide or ester bonds. The biologically-active molecule is released from the polymer at about pH 5–9 by the hydrolysis of the ester or amide bond that connects it to the monomers.

Examples of vinyl polymers with an hydroxyl-bearing functional group include 2-hydroxyethyl methacrylate, 2-hydroxypropyl methacrylate, p-styrene phenol, N-methacrylol serine, 2-hydroxyethyl methacrylamide, N-methacryloyl serine, methacryloyl 6-aminocaproyl serine, p-vinyl benzoyl 6-aminocaproyl serine, and the like.

The vinyl polymer with an imidazole-bearing functional group may be selected, for example, from N-methacrylol L-histidine, N-acrylol L-histidine, 4(5)-vinyl imidazole, N-methacrylol histamine, methacryloyl 6-aminocaproyl histidine, p-vinyl benzoyl 6-aminocaproyl histidine, and the like.

Useful vinyl polymers with a carboxyl-bearing functional group include, for example, acrylic acid, methacrylic acid, N-methacryloyl L-glutamic acid, N-methacryloyl aspartic acid, methacryloyl 6-aminoaproyl aspartic acid, p-vinyl benzoyl 6-aminocaproyl aspartic acid, and the like.

Examples of the substrate active ingredient-linked vinyl monomer ("S") include p-vinyl benzoic acid, acrylic acid, methacrylic acid, 2-hydroxyethyl methacrylate, p-vinyl phenol, p-vinyl amino styrene, and the like.

The process for the preparation of the polymer comprises:

a) bringing in juxtaposition, a vinyl monomer having a pendent functional group through which it is covalently bonded with the active ingredient, and another vinyl monomer bearing the catalytic group or $A_x$, or a pre-organised assembly of vinyl monomers bearing the catalytic groups (i.e., the assembly of the monomers $A_x$, $B_y$ and $C_z$ brought in proximity by complexation with cobalt);

b) polymerizing the resultant mixture with a hydrophilic monomer in the presence of a polymerization initiator, preferably at a temperature in the range of about 55°–75° C. under inert atmosphere or by Γ irradiation at a temperature in the range of about 40°–40° C.; and c) adding a buffer solution to the resultant composition at a temperature of about 25°–80° C., preferably about 25°–80° C., most preferably about 35°–40° C.

According to the invention, the polymeric composition may be prepared, for example, in the form of discs, dense microspheres, or deposited on the internal surfaces of porous spherical beads.

The active ingredient can be linked to vinyl monomers such as p-vinyl benzoic acid and 2-hydroxyethyl methacrylate, via —NH$_2$, —COOH or —OH pendent groups (i.e., functional group at the end of the vinyl monomer chain) using known synthetic procedures.

Examples of monomers bearing catalytic groups ($A_x$, $B_y$, $C_z$) include 1-vinyl imidazole, N-vinyl imidazole, 4-vinyl pyridine, N-methacryloyl L-histidine, N-acryloyl L-histidine, 4(5) vinyl imidazole, N-methacryloyl histidine, N-acryloyl histidine, N-vinyl pyridine, 2-vinyl pyridine, or similar nucleophilic groups such as methacryloyl aspartic acid, methacrylic acid, acrylic acid, acryloyl aspartic acid, and N-methyl hydroxamic acid.

The hydrophilic monomer is used in excess and does not participate in the hydrolysis of the ester or amide bond. Examples of hydrophilic monomers include 2-hydroxyethyl methacrylate, 2-hydroxypropyl methacrylate, acrylamide, N-isopropylacrylamide, methacrylamide, isopropyl acrylamide, methacrylic acid, acrylic acid, and the like. The monomers $A_x$, $B_y$, and $C_z$ play a role in the complex formation with the metal ion and hydrolysis of the amide or ester bond, but the hydrophilic monomer does not participate in complexation or hydrolysis. The catalytic group and the active ingredient-linked monomer can be brought in proximity by donor-acceptor complex formed by electrostatic interactions, hydrophobic interactions or by metal coordination. These can be affected by any conventional methods commonly employed.

The polymerization can be initiated thermally, or by $\Gamma$ irradiation in the absence of a chemical initiator. The polymerization can be carried out in the presence of metal ions such as $Ni^{++}$, $Co^{++}$, $Zn^{++}$, $Cu^{++}$, $Mg^{++}$, and similar transition metal ions used for metal coordination. The polymerization temperature may range from about 50°–90° C. for thermal polymerization and about 4°–40° C. for polymerization initiated by $\Gamma$ irradiation. Examples of polymerization initiators include azobisisobutyonitrile, t-butyl hydroperoxide, benzoyl peroxide, and the like. The inert atmosphere may be maintained using inert gases such as argon, nitrogen, neon, krypton, helium, and the like. The duration of polymerization time may be varied from 6–24 hours. The metal ion can be extracted using dilute HCl, ethylenediamine tetraacetic acid, or methanol containing 2,2-bipyridyl, or 1,10-phenanthroline. The unreacted monomers can be extracted using solvents such as methanol, acetone, ethanol, dichloromethane, chloroform, ethyl acetate, carbon tetrachloride, methyl ethyl ketone, methyl acetate, methyl isobutyl ketone, and the like.

Examples of active ingredients include p-nitrophenol, p-nitroaniline, p-nitrobenzoic acid, p-aminobenzoic acid, paracetamol, chloroamphenicol, ibuprofen, salicylic acid, p-methoxyphenol, metronidazole, daunomycin, pholcodine, theophylline, 5-hydroxyquinoline, naproxen, ketoprofen, 5-fluorouracil, napthyl acetic acid, sulfanilamide, 8-hydroxyquinoline, niclosamide, metribuzin, nicotinic acid, 2,4-dichlorophenoxy acetic acid, 2,4,5-trichlorophenoxy propionic acid, or other active ingredient with appropriate functional groups to link to the pendent chain.

The polymer composition contains monomers comprising imidazole, carboxyl and hydroxyl groups. The ester- or amide-bearing monomer is also incorporated in the structure by polymerization and is therefore a part of the polymer structure. The polymer composition is defined by $A_x$, $B_y$, $C_z$ and $S_q$ wherein A is an imidazole group-bearing monomer, B is an hydroxyl group-bearing monomer, C is a carboxyl group-bearing monomer, and S is a monomer bearing an ester or amide group in the pendent chain, such that $x+y+z+q=1$. The value of x and s are defined by $0<x<1$ and $0<q<1$, and y and z can vary between 0 and 1.

The presence of the hydroxyl and carboxyl groups enhances the catalytic activity of the imidazole group. However, in absence of those groups, imidazole can exhibit catalytic activity although lower than that in the presence of hydroxyl and carboxyl groups.

It is also noted that the substrate is a part of the polymer structure and ideally the ratio of moles of the substrate to moles of the catalytic group-bearing vinyl monomers does not exceed 1. The term "catalytic group" means the functional group or groups that are involved in the catalytic hydrolysis of the active ingredient linked monomer to release the free active ingredient.

The process of the invention involves complexation of the imidazole- and carboxyl-bearing monomer along with a template/imprint molecule in the presence of the metal ion. This complex is then mixed with a hydroxyl-bearing monomer. The catalytic activity arises from the nucleophility of the imidazole group and can be enhanced by the carboxyl and/or by the hydroxyl group.

The template/imprint molecule is a molecule which structure is identical to the active ingredient linked monomer but which cannot be polymerized, and has a functional group that can bind to the metal ion. Such a molecule is used during complex formation with the metal ion along with the monomer bearing the catalytic group. After polymerization is complete, the template molecule and the metal ion are leached out leaving a cavity which is the size of the template/imprint molecule. The active ingredient linked monomer is then sorbed into the cavities and polymerized by gamma irradiation.

The invention will now be described in greater details in the following examples which are provided to illustrate the invention and should not therefore be construed to limit the scope of the present invention.

EXAMPLE 1

P-vinyl benzoic acid was esterified with p-nitrophenol to give p-vinyl benzoate. 0.5 gm p-nitrophenyl p-vinyl benzoate, 0.174 gm 1-vinyl imidazole and 4.32 gm 2-hydroxyethyl methacrylate were placed in a test tube (15×150 mm), 0.8 ml t-butyl hydroperoxide was added, and the tube was purged with nitrogen for 10 minutes. Polymerization was carried out at 65° C. for 16 hours. The polymer was isolated in the form of a rod by breaking the test tube. The yield obtained was 4.8 gm. The rod was then cut into discs of 0.09–0.11 cm thickness on a lathe. Any unreacted monomers were extracted by soaking the discs in acetone for 12 hours and then drying the discs in a vacuum oven at 60° C.

The polymer discs were weighed and then dipped in 100 ml phosphate buffer (0.01M) of pH 8 in two jacketed vessels. The medium was constantly stirred using a magnetic stirrer. The temperature was maintained at 37° C. The buffer was changed every 12 hours. After every 4 hours, 2 ml samples were withdrawn and analyzed by U.V. spectrophotometer for p-nitro phenol at 400 nm. The volume was maintained by replacing 2 ml fresh buffer. It was observed that in 60 hours, 50% of p-nitrophenol was released.

EXAMPLE 2

0.5 gm p-nitrophenyl p-vinyl benzoate, 0.414 gm N-methacryloyl histidine and 4.08 gm 2-hydroxy ethyl methacrylate were placed in a test tube, 0.8 ml t-butyl hydroperoxide was added and the tube was purged with nitrogen for 10 minutes. Polymerization was carried out at 65° C. for 16 hours. The polymer was isolated by breaking the test tube. The yield obtained was 4.8 gm. The rod was then cut into discs of 0.09–0.11 cm on a lathe. The unreacted monomers were extracted by soaking the discs in acetone for 12 hours, and drying them in a vacuum oven at 60° C.

A polymer disc was weighed and dipped into 100 ml phosphate buffer (0.01M), pH 8, in a jacketed vessel. The reaction medium was constantly stirred using a magnetic stirrer. The temperature was maintained at 37° C. The medium was changed after every 6 hours. After every 2 hours, a 2-ml sample was withdrawn and analyzed using a UV spectrophotometer at 400 nm. The volume of the medium was maintained at 100 ml by replacing 2-ml fresh phosphate buffer. Within 40 hours, 60% of the p-nitrophenol was released.

EXAMPLE 3

P-vinyl benzoyl chloride was esterified with p-nitrophenol using triethylamine to give p-vinyl benzoate. 0.5 gm p-nitrophenyl p-vinyl benzoate, 0.174 gm 1-vinyl imidazole, and 4.32 gm 2-hydroxyethyl methacrylate were placed in a test tube (15×150 mm). 0.8 ml t-butyl hydroperoxide was added and the tube was purged with nitrogen for 10 minutes. Polymerization was carried out at 65° C. for 16 hours. The polymer was isolated by breaking the test tube. The yield obtained was 4.8 gm. The rod was then cut into discs of 0.09–0.11 cm thickness on a lathe. The unreacted monomers, if any, were extracted by soaking the discs in acetone for 12 hours and then drying them in a vacuum oven at 60° C. Six polymer discs were weighed and then dipped into 100 ml buffer of pH 7.4, 6.8, 5.5, 4.0, 3.2 at 37° C. and the p-nitro phenol released was analyzed at 400 nm at pH 7.4, 6.8, 5.6 and at 314 nm at pH 3.2 and 1.2. It was observed that at the end of 60 hours the amount of p-nitrophenol released at pH 7.4, 6.8, 5.5, 3.2 and 1.2 was 42%, 35%, 24%, 5% and 0.5%, respectively.

EXAMPLE 4

1.0 gm p-nitrophenyl p-vinyl benzoate, 3.82 gm 2-hydroxyethyl methacrylate and 0.174 gm 1-vinyl imidazole were placed in a test tube (15×150 mm), 0.8 ml t-butyl hydroperoxide was added, and the tube was purged with nitrogen for 10 minutes. The polymerization was carried out at 65° C. for 16 hours. The polymer was isolated by breaking the test tube. Yield was 4.87 gm. The rod was then cut into discs of thickness 0.09–0.11 cm, on a lathe. The unreacted monomers were extracted by soaking the discs in acetone for 12 hours. The discs were dried in a vacuum oven at 60° C. A polymer disc was weighed and dipped in phosphate buffer (0.01M) of pH 8.0 in a jacketed vessel maintained at 37° C. and with constant stirring. The p-nitrophenol that was released was monitored at 400 nm on a spectrophotometer. It was observed that in 60 hours, 35% of the p-nitrophenol was released, and in 140 hours, 42% of p-nitrophenol was released.

EXAMPLE 5

P-vinyl benzoyl chloride was esterified with 2,4-dinitrophenol using standard synthetic methods (triethylamine) to give 2,4 dinitrophenyl p-vinyl benzoate, 0.5 gm 2,4-dinitrophenyl p-vinyl benzoate, 0.149 gm 1-vinyl imidazole, and 4.35 gm 2-hydroxyethyl methacrylate were placed in a test tube (15×150 mm). 0.8 ml t-butyl hydroperoxide was added and the tube was purged with nitrogen for 10 minutes. Polymerization was carried out at 65° C. for 16 hours. The polymer was isolated by breaking the test tube. The rod was cut into discs of 0.09–0.11 cm thickness on a lathe. The unreacted monomers were extracted by soaking the discs in acetone for 12 hours, and then drying them in a vacuum oven at 60° C. The polymer discs were weighed and then dipped in 100 ml phosphate buffer (0.001M), pH 8, in two jacketed vessels. The medium was constantly stirred using a magnetic stirrer. The temperature was maintained at 37° C. The buffer was changed every 12 hours. After every 4 hours, 2-ml samples were withdrawn and analyzed using a U.V. spectrophotometer for 2,4-dinitrophenol at 320 nm. The volume was maintained by replacing 2 ml fresh buffer. The release of 2,4-dinitrophenol was followed until all the 2,4-dinitrophenol was released. It was observed that in 48 hours, 68% of 2,4-dinitrophenol was released.

EXAMPLE 6

P-nitrobenzoic acid was esterified with 2-hydroxyethyl methacrylate to give 2-methacryloyl ethyl p-nitrobenzoate. A print molecule N-isobutyryl ethyl nicotinate, which is structurally identical to 2-methacryloyl ethyl p-nitrobenzoate, was used. 0.750 gm (0.0031 mol) N-isobutyryl ethyl nicotinate, 0.30 gm N-vinyl imidazole and 0.184 gm $CoCl_2.4H_2O$ were added to 5 ml methanol and the solution was stirred at room temperature for 1 hour. Methanol was then evaporated under reduced pressure. The complex was diluted with 3,766 gm 2-hydroxyethyl methacrylate. 0.8 ml t-butyl hydroperoxide was added and the test tube was purged with nitrogen for 10 minutes. Polymerization was carried out at 65° C. for 16 hours. The polymer was isolated by breaking the test tube. The yield obtained was 4.75 gm. The rod was then cut into discs of 0.09–0.11 cm thickness on a lathe. The print molecule and cobalt were extracted in methanol containing 1% 2,2 bipyridyl and then with dilute hydrochloric acid. These polymer discs were then soaked with dilute hydrochloric acid. These polymer discs were then soaked in an acetone solution of 2-methacryloyl ethyl p-nitrobenzoate for 24 hours. The monomer that was sorbed in the matrix was polymerized by $\Gamma$ irradiation from a $Co^{60}$ source (0.25 Mrad/hr) for 6 hours. The unreacted monomer was extracted in acetone for 12 hours.

The polymer disc was weighed and then dipped in 100 ml phosphate buffer (0.01M) of pH=8.0. The temperature was maintained at 37° C. The buffer was changed every 24 hours. After every 4 hours, a 2-ml sample was withdrawn and analyzed by U.V. spectrophotometer for p-nitro benzoic acid at 270 nm. The volume was maintained by replacing 2 ml fresh buffer. 50% of p-nitrobenzoic acid was released in 75 hours.

EXAMPLE 7

Methacryloyl chloride was reacted with β-alanine to give N-methacryloyl β-alanine which was further reacted with p-nitro aniline to obtain N-methacryloyl β-alanyl p-nitro anilide. N-isobutyryl β-alanyl 2-amino pyridine was used as the print molecule, 0.5 gm (0.0021 mol) N-isobutyryl β-alanyl 2-amino pyridine, 0.468 gm (0.0021 mol) N-methacryloyl histidine, and 0.124 gm (0.0021 mol) $CoCl_2.6H_2O$ were placed in 5 ml methanol and stirred for 1 hour. Methanol was evaporated under reduced pressure. The complex was diluted with 3.9 gm 2-hydroxyethyl methacrylate, 0.8 ml t-butyl hydroperoxide was added, and the mixture polymerized at 65° C. for 16 hours.

The polymer was isolated and cut into discs of thickness 0.09–0.11 cm, on a lathe. Cobalt chloride and N-isobutyryl β-isobytyryl β-alanyl 2-amino pyridine were extracted in methanol containing 1% 2,2-bipyridyl. The discs were then soaked in an acetone solution of N-isobutyryl β-ananyl p-nitro anilide for 24 hours. The monomer that was sorbed was polymerized by $\Gamma$ irradiation from a $Co^{60}$ source for 6 hours. The unreacted monomer was extracted in acetone. A polymer disc was weighed and dipped in 100 ml phosphate buffer (0.01M), pH 8, in a jacketed vessel maintained at 37° C. The release of p-nitroaniline was followed at 380 nm on a U.V. spectrophotometer. 60% of p-nitro aniline was released in 60 hours.

EXAMPLE 8

0.49 gm methacryloyl L-histidine, 0.189 gm methacrylic acid, 0.5 gm $CoCl_2.6H_2O$ and 0.5 gm isobutyryl ethyl nicotinate (print molecule) were placed in a 25-ml beaker and stirred for 1 hour to form a blue colored complex. This mixture was then placed in a test tube and methanol was evaporated under reduced pressure. 3.3 gm 2-hydroxyethyl methacrylate was added and polymerized at 65° C. for 16 hours. The polymer was isolated by breaking the test tube. The yield obtained was 4.68 gm.

$CoCl_2$ was extracted from the polymer discs in methanol. The print molecule was also extracted simultaneously. The discs were washed thoroughly in dilute acid and then dried in a vacuum oven at 60° C.

These polymer discs were then dipped in an acetone solution of 2-methacryloyl ethyl p-nitro benzoate for 12 hours. After 12 hours, the discs were removed and the monomer that was absorbed was polymerized using irradiation (0.25 Mrad/hr) from a $Co^{60}$ source for 8 hours. The unreacted monomer was extracted from the discs using acetone and the disc were dried at 60° C.

Figure 2:
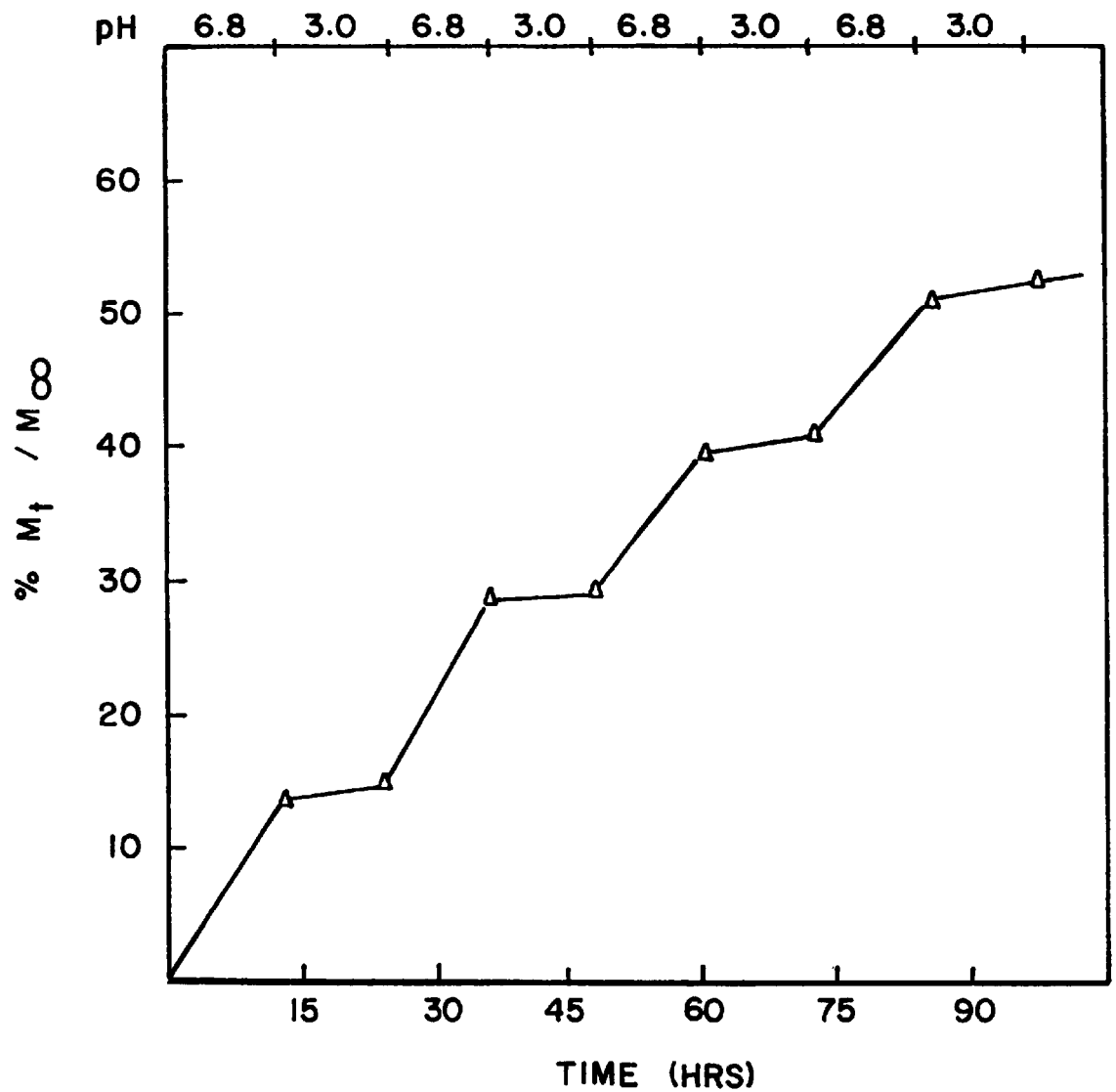
FIG. 2 is a graphical representation of the release of p-nitro benzoic acid as reported in example 8 of the specification.

The discs were dipped in 100 ml phosphate buffer of pH 6.8 in a jacketed vessel maintained at 37° C. for the first 12 hours, and then were transferred to another vessel having 100 ml citrate buffer, pH 2, at 37° C. for the next 12 hours. The release of p-nitro benzoic acid in both cases was followed at 270 nm on a U.V. spectrophotometer. The percentage release was plotted against time and is shown in FIG. 2 of the drawings accompanying this specification.

EXAMPLE 9

P-amino benzoic acid was esterified with 2-hydroxyethyl methacrylate to give 2-methacryloyl ethyl p-amino benzoate. 0.5 gm 2-methacryloyl hydroxyethyl p-amino benzoate was placed in a 25-ml beaker. To this, 0.119 gm $CoCl_2.6H_2O$ and 5 ml methanol were added along with 0.188 gm 1-vinyl imidazole. The mixture was stirred for 1 hour to give a green-blue colored complex. This was then added to a test tube, and methanol was evaporated under reduced pressure. 4.19 gm 2-hydroxyethyl methacrylate and 0.8 ml t-butyl hydroperoxide were added and the tube was purged with nitrogen for 10 minutes. Polymerization was carried out at 65° C. for 16 hours. The yield obtained was 4.7 gms. The polymer rod was then cut into discs of 0.09–0.11 cm thickness of a lathe. The polymer discs were dipped in a 1% bypyridyl solution in methanol for 12 hours to extract all the $Co^{++}$ and then dried at 60° C.

Three polymer discs were weighed and dipped in 100 ml buffer at pH 8, 6.8, 3 and 1.2, respectively. The temperature was maintained at 37° C. The release of p-amino benzoic acid was followed at 265 nm on a U.V. spectrophotometer. It was observed that after 7 days, 30%, 22%, 2.5%, and 0.01% p-aminobenzoic acid was released at pH 8, 6.8, 3 and 1.3, respectively.

EXAMPLE 10

Methacryloyl chloride was reacted with 6-amino caproic acid to give N-methacryloyl 6-amino caproic acid. This was then esterified with p-nitrophenol using standard synthetic methods to give N-methacryloyl 6-amino caproyl p-nitrophenol. 0.5 gm (0.0018 mol) N-isobutyryl 6-amino osproyl 2-amino pyridine, 0.4 gm N-methacryloyl histidine and 0.1071 gm $CoCl_2.6H_2O$ were dissolved in 5 ml methanol and stirred for 1 hour. Methanol was then removed under reduced pressure. This was further diluted with 3.5 gm 2-hydroxyethyl methacrylate and 0.5 ml ethylene glycol dimethacrylate, and 100 mg azobisisobutyronitrile.

In a three-necked round bottom flask, 47 ml 37% NaCl solution was added. To it, 2 gm $MgCl_2.6H_2O$ and 3 ml 1N NaOH were added. Nitrogen was passed through the solution for 15 minutes. The monomer mixture was also purged with nitrogen for 10 minutes, and added dropwise to the $Mg(OH)_2$ suspension at 75° C. with a stirring speed of 1000 rpm. Microspheres were formed immediately which hardened after 3 hours. They were separated out by filtration. Cobalt and the N-isobutyryl 6-aminocaproyl 2-amino pyridine was extracted by washing the spheres with methanolic solution of 2.2 bipyridyl. The spheres were dried in a vacuum oven for 24 hours. Spheres in the size range 37–45$\mu$ were chosen for further study. Yield obtained was 4 gm.

1 gm microspheres were soaked in an acetone solution of N-methacryloyl 6-amino caproyl p-nitrophenol for 24 hours. The monomer that was sorbed in the spheres was polymerized by exposing to $\Gamma$ irradiation from a $Co^{60}$ source (0.25 Mrad/hr) for 6 hours. The unreacted monomer was extracted in acetone.

100 mg microspheres were dipped in 100 ml phosphate buffer (0.01M) of pH=8, 7.4, 6.8, 3.2 and 1.2 in jacketed vessels maintained at 37° C. that was constantly stirred. After every 15 minutes, 2 ml of buffer was removed and analyzed for the p-nitrophenol released. 2 ml fresh buffer was added to the reaction medium to maintain the volume. It was observed that in 100 minutes, 62%, 50%, 40%, 10% and 1% of p-nitrophenol was released at pH 8.0, 7.4, 6.8, 3.2 and 1.2, respectively.

The nature of the polymeric composition of the present invention, which is used for the controlled release of an active ingredient incorporated therein in response to a particular range of pH is given in Table 1.

TABLE 1

| Formulation | Active ingredient | Time | pH | % Hydrolysis |
|---|---|---|---|---|
| Disc | p-nitrophenol | 60 hrs | 8 | 50 |
| Disc | p-nitrophenol | 40 hrs | 8 | 60 |
| Disc | p-nitrophenol | 60 hrs | 7.4 | 42 |
| Disc | 2,4 dinitrophenol | 48 hrs | 8 | 68 |
| Disc | p-nitrobenzoic acid | 75 hrs | 8 | 50 |
| Disc | p-nitroaniline | 60 hrs | 8 | 60 |
| Disc | p-amino benzoic acid | 7 days | 8 | 30 |
| Disc | p-amino benzoic acid | 7 days | 6.8 | 22 |
| Disc | p-amino benzoic acid | 7 days | 3.0 | 2.5 |
| Disc | p-amino benzoic acid | 7 days | 1.2 | 0.1 |
| Microspheres | p-nitrophenol | 100 min | 8.0 | 62 |
| Microspheres | p-nitrophenol | 100 min | 7.4 | 50 |
| Microspheres | p-nitrophenol | 100 min | 6.8 | 40 |
| Microspheres | p-nitrophenol | 100 min | 3.2 | 10 |
| Microspheres | p-nitrophenol | 100 min | 1.2 | 1 |

The polymeric compositions described herein offer the following advantages:

1. The cleavage of the active ingredient-polymer bond can take place preferably in the temperature range of about 25°–40° and a pH range of about pH 5 to 7.5.
2. Polymers used in the process of the invention are non-toxic and biocompatible.
3. Active ingredients such as drugs, pesticides, insecticides, herbicides, and fungicides having functional groups like —OH, —COOH, or —NH₂ can be incorporated.

4. A controlled release polymer composition prepared according to the process of the invention releases the active ingredient in a controlled manner in response to the pH of the medium. This is because the catalytic activity of the polymer which arises from the proximity of the functional groups, depends on the pH. At pH below 3.5, the catalytic activity of the polymer is lost.

5. The process is useful for drug delivery to the gastrointestine where the pH is close to pH 7.0. In the stomach, where the pH is highly acidic pH (1.5–2.5), no release takes place.

6. The polymer composition can be administered as discs, tablets, beads, and the like, either in a dense form or in a porous form.

We claim:

1. A polymer for the controlled release of an active ingredient, the polymer having the general formula $A_xB_yC_zS_q$ wherein A is an imidazole group-bearing vinyl monomer, B is a hydroxyl group-bearing vinyl monomer, C is a carboxyl group-bearing vinyl monomer, and S is a vinyl monomer covalently bonded to an active ingredient through an amide or an ester; and x+y+z+q=1; and x, y, z, q can vary such that 0<x<1, and 0<q<1, and y and z can vary between 0 to 1.

2. The polymer according to claim 1, wherein the active ingredient is selected from the group consisting of a drug, insecticide, fungicide, herbicide, pesticide, and weedicide.

3. The polymer according to claim 1, wherein the active ingredient is linked to the S vinyl monomer through an —OH, —COOH or —NH$_2$ group.

4. The polymer according to claim 1, wherein the (s) vinyl monomer is selected from the group consisting of 1-vinyl imidazole, 4-vinyl pyridine, N-methacryloyl L-histidine, and N-acryloyl L-histidine.

5. The polymer according to claim 1, wherein the hydroxyl group-bearing vinyl monomer (B) is selected from the group consisting of 2-hydroxyethyl methacrylate, 2-hydroxypropyl methacrylate, p-styrene phenol, N-methacryloyl serine, 2-hydroxyethyl methacrylamide, N-methacryloyl serine, methacryloyl 6-aminocaproyl serine, and p-vinyl benzoyl 6-aminocaproyl serine.

6. The polymer according to claim 1, wherein the imidazole group-bearing vinyl monomer (A) is selected from the group consisting of N-methacryloyl L-histidine, N-acryloyl L-histidine, 4(5)-vinyl imidazole, N-methacryloyl histamine, methacryloyl 6-aminocaproyl histidine, and p-vinyl benzoyl 6-aminocaproyl histidine.

7. The polymer according to claim 1, wherein the carboxyl group-bearing vinyl monomer (C) is selected from the group consisting of acrylic acid, methacrylic acid, N-methacryloyl L-glutamic acid, N-methacryloyl aspartic acid, methacryloyl 6-aminoaproyl aspartic acid, and p-vinyl benzoyl 6-aminocaproyl aspartic acid.

8. The polymer according to claim 1, wherein the active ingredient is releasable from the polymer at about pH 5–10.

9. A process of preparing a polymer as recited in claim 1, comprising:

(a) bringing into juxtaposition, said vinyl monomers releasably linked through a pendent group to an active ingredient with (i) a second vinyl monomer bearing a catalytic group, or (ii) a preorganized assembly of vinyl monomers bearing catalytic groups to form a mixture;

(b) in the presence of a polymerization initiator at a temperature of about 55°–75° C. under an inert atmosphere, or (ii) by Γ irradiation at a temperature of about 4°–40° C.; and (c) combining the polymerized mixture with an aqueous medium, at a temperature of about 25°–80° C.

10. The process of claim 9, wherein the active ingredient is selected from the group consisting of a drug, insecticide, fungicide, herbicide, pesticide, and weedicide.

11. The process of claim 9, wherein the active ingredient is linked to the S vinyl monomer through an —OH, —COOH or —NH$_2$ group via an amide or ester bond.

12. The process of claim 9, wherein the first vinyl monomer is selected from the group consisting of p-nitrophenyl p-vinyl benzoate, 2,4 dinitrophenyl p-vinyl benzoate, 2-methylacryloyl ethyl p-nitro benzoate, 2-methacryloyl ethyl p-amino benzoate, N-methacryloyl 6-amino caproyl p-nitrophenol, and N-methacryloyl B-alanine p-nitroanilide.

13. The process of claim 9, wherein the catalytic group-bearing vinyl monomer in step (a) is selected from the group consisting of N-vinyl imidazole, 4(5) vinyl imidazole, N-methacryloyl histidine, N-acryloyl histidine, N-vinyl pyridine, 2-vinyl pyridine, methacryloyl aspartic acid, methacrylic acid, acrylic acid, acryloyl aspartic acid, N-methyl hydroxamic acid, 1-vinyl imidazole, 4-vinyl pyridine, N-methacryloyl L-histidine, and N-acryloyl L-histidine.

14. The process of claim 9, wherein the hydrophilic monomer of step (b) is selected from the group consisting 2-hydroxyethyl methacrylate, 2-hydroxypropyl methacrylate, acrylamide, methacrylamide, N-isopropyl acrylamide, isopropyl acrylamide, methacrylic acid, and acrylic acid.

15. The process of claim 9, wherein step (a) is effected by donor-acceptor complex formation by electrostatic interaction, hydrophobic interaction, metal coordination, or a combination thereof.

16. The process of claim 9, wherein polymerizing step (b) is carried out in the presence of a metal ion selected from the group consisting of $Co^{++}$, $Ni^{++}$, $Cu^{++}$, $Zn^{++}$, $Mg^{++}$, $Mn^{++}$, and $Fe^{+++}$.

17. The process of claim 9, wherein polymerizing step (b) is carried out by thermal polymerization at a temperature of about 50°–90° C., or by irradiation at about 4°–40° C.

18. The process of claim 9, wherein polymerizing step (b) is initiated thermally or by irradiation in the absence of a chemical initiator.

19. The process of claim 9, wherein polymerization step (b) is effected for about 6–24 hours.

20. The process of claim 9, wherein polymerizing step (b) employs a free radical initiator selected from the group consisting of azobisisobutyronitrile and t-butyl hydroperoxide.

21. The process of claim 9, wherein the inert atmosphere is maintained by an inert gas selected from the group consisting of nitrogen, argon, helium, neon, and carbon dioxide.

22. The process of claim 9, further comprising removing unreacted monomers by combining the mixture with a solvent selected from the group consisting of methanol, acetone, ethanol, propanol, butanol, dichloromethane, ethyl acetate, methyl acetate, carbon tetrachloride, methyl ethyl ketone, and methyl isobutyl ketone.

23. The process of claim 9, wherein the active ingredient is a drug selected from the group consisting of p-nitrophenol p-nitroaniline, p-nitro benzoic acid, p-amino benzoic acid, paracetamol, chloroamphenicol, ibuprofen, salicylic acid, p-methoxy phenol, metronidazole, daunomycin, pholcodine, theophylline, 5-fluorouracil, naproxen, ketoprogen, salicylic acid, sulfanilamide, 8-hydroxy quinoline, naphthyl acetic acid, niclosamide, metribuzin, nicotinic acid, 2,4-dichloro phenoxy acetic acid, and 2,4,5-trichloro phenoxy propionic acid.

* * * * *